(12) United States Patent
Ueno

(10) Patent No.: US 11,795,137 B2
(45) Date of Patent: Oct. 24, 2023

(54) MANUFACTURING METHOD OF NITRILE COMPOUND

(71) Applicant: Mitsubishi Gas Chemical Company, Inc., Chiyoda-ku (JP)

(72) Inventor: Masayoshi Ueno, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 270 days.

(21) Appl. No.: 17/431,284

(22) PCT Filed: Mar. 25, 2020

(86) PCT No.: PCT/JP2020/013435
§ 371 (c)(1),
(2) Date: Aug. 16, 2021

(87) PCT Pub. No.: WO2020/203581
PCT Pub. Date: Oct. 8, 2020

(65) Prior Publication Data
US 2022/0135515 A1    May 5, 2022

(30) Foreign Application Priority Data
Mar. 29, 2019  (JP) ................................. 2019-065750

(51) Int. Cl.
*C07C 253/28*    (2006.01)
(52) U.S. Cl.
CPC .................................. *C07C 253/28* (2013.01)
(58) Field of Classification Search
None
See application file for complete search history.

(56) References Cited

U.S. PATENT DOCUMENTS

| | | |
|---|---|---|
| 4,134,910 A | 1/1979 | Barchas et al. |
| 2001/0007039 A1 | 7/2001 | Shitara et al. |
| 2003/0114701 A1 | 6/2003 | Nakamura et al. |

FOREIGN PATENT DOCUMENTS

| | | |
|---|---|---|
| CN | 1302285 A | 7/2001 |
| JP | 54-16445 A | 2/1979 |
| JP | 2001-181253 A | 7/2001 |
| JP | 2003-238511 A | 8/2003 |
| JP | 2015-98455 A | 5/2015 |

OTHER PUBLICATIONS

International Search Report dated Jun. 9, 2020 in PCT/jP2020/013435 filed Mar. 25, 2020.

*Primary Examiner* — Samantha L Shterengarts
(74) *Attorney, Agent, or Firm* — Oblon, McClelland, Maier & Neustadt, L.L.P.

(57) ABSTRACT

A manufacturing method of a nitrile compound comprising a first step of introducing a raw material gas containing a cyclic compound having an organic substituent, ammonia, and air into a reactor and reacting the raw material gas in the presence of a catalyst to generate the nitrile compound, a second step of discharging a reacted gas from the reactor and separating the nitrile compound from the reacted gas, and a third step of collecting mist from a first residual gas obtained by separating the nitrile compound from the reacted gas to remove water and ammonium carbonate in the first residual gas.

20 Claims, 2 Drawing Sheets

MANUFACTURING METHOD OF NITRILE COMPOUND

CROSS-REFERENCE TO RELATED APPLICATIONS

The present application is a 35 U.S.C. § 371 national stage application of International patent application PCT/JP2020/013435, filed Mar. 25, 2020, which is based on and claims the benefit of priority to Japanese Application No. 2019-065750, filed on Mar. 29, 2019. The entire contents of these applications are incorporated herein by reference.

TECHNICAL FIELD

The present invention relates to a manufacturing method of a nitrile compound such as a carbocyclic nitrile compound or a heterocyclic nitrile compound by ammoxidation reaction using a cyclic compound such as a carbocyclic compound or a heterocyclic compound having an organic substituent as a raw material.

BACKGROUND ART

A carbocyclic nitrile compound is useful as a raw material for manufacturing of a synthetic resin, an agricultural chemical, etc. and an intermediate raw material of an amine, an isocyanate, etc. On the other hand, a heterocyclic nitrile compound is useful as an intermediate raw material of a medicament, a feed additive, a food additive, etc. A method of reacting an organic compound such as a carbocyclic compound or a heterocyclic compound (hereinafter sometimes referred to as a "cyclic compound") having an organic substituent with ammonia and an oxygen-containing gas is referred to as "ammoxidation", and generally a nitrile compound is manufactured by gas phase catalytic reaction. As a catalyst used for ammoxidation, a catalyst containing vanadium, molybdenum, iron, etc. is known.

In ammoxidation, a nitrile compound which is the objective substance is separated from a reacted gas and recovered; however, the residual gas after separating a nitrile compound comprises water, nitrogen, oxygen, ammonia, carbon dioxide, carbon monoxide, an unreacted carbocyclic compound or heterocyclic compound, etc. (for example, see Patent Literatures 1 and 2 below).

CITATION LIST

Patent Literature

Patent Literature 1: Japanese Patent Laid-Open No. 2003-238511
Patent Literature 2: Japanese Patent Laid-Open No. 54-16445

SUMMARY OF INVENTION

Technical Problem

It is generally known that, In the condition in which carbon dioxide and ammonia exist, ammonium carbonate is generated which is solid at room temperature. There is a concern about clogging of the line due to deposition of ammonium carbonate in a place where the temperature is lower than or equal to the melting point of ammonium carbonate.

In ammoxidation reaction, reaction conditions such as composition of a feed gas, contact time, and reaction temperature are important factors which determine the yield of the nitrile compound and productivity, and are generally controlled strictly. However, when a nitrile compound is manufactured by ammoxidation, air is used as an oxygen source in industrial manufacturing, but the oxygen concentration in the air is not constant in the case of using air as an oxygen source.

Therefore, as a method of maintaining the oxygen concentration at a constant level without adding a facility for supplying pure oxygen gas, Patent Literature 1 proposes a method in which a residual gas obtained by separating the nitrile compound from a reacted gas is resupplied to a reactor in the proportion of 10 to 60 vol % based on a raw material gas freshly supplied to the reactor and comprising the carbocyclic compound or heterocyclic compound, ammonia, and air. However, in the above method, the residual gas obtained by separating the nitrile compound from the reacted gas is returned to the reactor for the purpose of maintaining the oxygen concentration at a constant level, and thus when ammonium carbonate in the residual gas deposits and clogs the line, the amount of the residual gas supplied is difficult to control, and maintaining the target oxygen concentration at a constant level may be difficult.

On the other hand, there was a concern about increase in size of the facility when a cooling apparatus, etc. are additionally installed for recovering the ammonium carbonate. Furthermore, installation of a large-size cooling apparatus having high performance causes a problem in cost as well.

The object of the present invention is to provide a manufacturing method of a nitrile compound which enables suppression of deposition of ammonium carbonate and stable manufacturing of a nitrile compound, in order to solve the above problems.

Solution to Problem

The present inventors engaged in diligent study and consequently achieved the present invention by discovering that in the method of synthesizing a nitrile compound such as a carbocyclic nitrile compound or a heterocyclic nitrile compound by ammoxidation reaction using a cyclic compound such as a carbocyclic compound or a heterocyclic compound having an organic substituent as a raw material, ammonium carbonate contained in a residual gas together with water can be removed by collecting mist from the residual gas without attempting increase in size of a facility.

<1> A manufacturing method of a nitrile compound comprising
a first step of introducing a raw material gas containing a cyclic compound having an organic substituent, ammonia, and air into a reactor and reacting the raw material gas in the presence of a catalyst to generate the nitrile compound,
a second step of discharging a reacted gas from the reactor and separating the nitrile compound form the reacted gas, and
a third step of collecting mist from a first residual gas obtained by separating the nitrile compound from the reacted gas to remove water and ammonium carbonate in the first residual gas.
<2> The manufacturing method of a nitrile compound according to the above <1>, wherein the mist is removed from the first residual gas by a mist eliminator in the third step.

<3> The manufacturing method of a nitrile compound according to the above <2>, wherein the mist eliminator is a Vane-type mist eliminator.

<4> The manufacturing method of a nitrile compound according to any of the above <1> to <3>, wherein the cyclic compound is a carbocyclic compound or a heterocyclic compound.

<5> The manufacturing method of a nitrile compound according to any of the above <1> to <4>, wherein the nitrile compound is an aromatic nitrile compound.

<6> The manufacturing method of a nitrile compound according to any of the above <1> to <5>, wherein the cyclic compound is meta-xylene, and the nitrile compound is isophthalonitrile.

<7> The manufacturing method of a nitrile compound according to any of the above <1> to <6>, wherein a second residual gas obtained by removing the water and the ammonium carbonate from the first residual gas is resupplied to the reactor.

<8> The manufacturing method of a nitrile compound according to the above <7>, wherein an amount of the second residual gas supplied to the reactor is 10 to 60 vol % based on the raw material gas freshly supplied through an inlet of the reactor.

Advantageous Effect of Invention

According to the present invention, a manufacturing method of a nitrile compound which enables suppression of deposition of ammonium carbonate and stable manufacturing of a nitrile compound can be provided.

DESCRIPTION OF EMBODIMENTS

Figure 1:
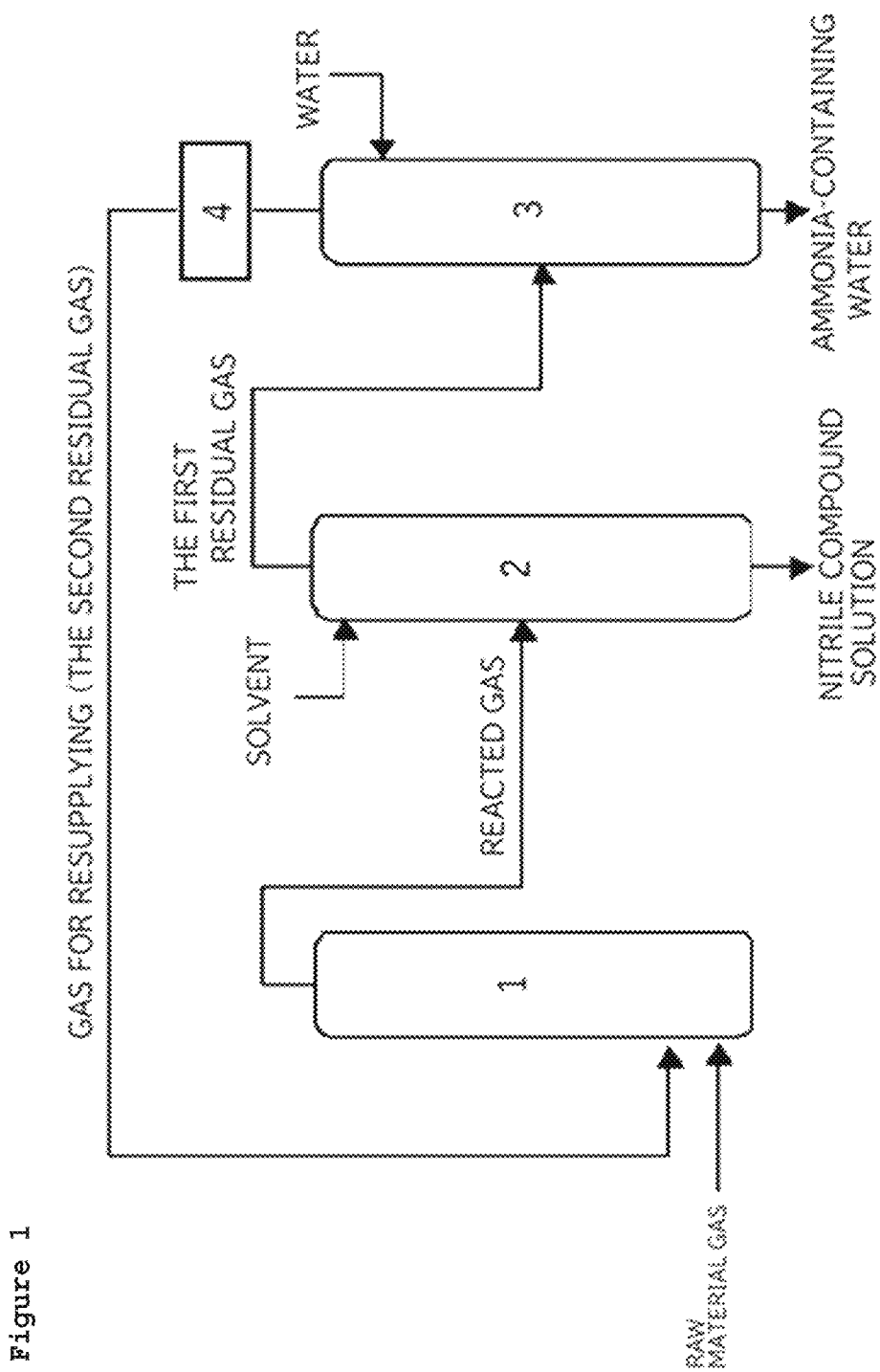
FIG. 1 is a schematic view showing an example of the manufacturing process of a nitrile compound of the present embodiment.

Hereinafter, the present invention will be described in detail, but the present invention is not limited to each embodiment shown below.

<Manufacturing Method of Nitrile Compound>

The manufacturing method of a nitrile compound of the present embodiment (hereinafter sometimes simply referred to as "the manufacturing method of the present embodiment") comprises a first step of introducing a raw material gas containing a cyclic compound having an organic substituent, ammonia, and air into a reactor and reacting the raw material gas in the presence of a catalyst to generate a nitrile compound, a second step of discharging a reacted gas from the reactor and separating the nitrile compound form the reacted gas, a third step of collecting mist from a first residual gas obtained by separating the nitrile compound from the reacted gas to remove water and ammonium carbonate in the first residual gas.

According to the manufacturing method of the present embodiment, in the third step, ammonium carbonate dissolved in water in the mist can be removed from the first residual gas by collecting the mist in the gas from the first residual gas using a mist eliminator, etc. Thus, since ammonium carbonate in the residual gas which is to be resupplied to the reactor can be removed, clogging of the line due to deposition of ammonium carbonate can be prevented in the resupply line of the residual gas. Therefore, according to the manufacturing method of the present embodiment, it is possible to maintain the oxygen concentration in the gas supplied to the reactor at a constant level and to stably manufacture the nitrile compound.

[First Step]

The first step is a step of introducing a raw material gas containing a cyclic compound having an organic substituent, ammonia, and air into a reactor and reacting the raw material gas in the presence of a catalyst to generate a nitrile compound. In the present embodiment, a "raw material gas" refers to a gas supplied to a reactor, and contains at least a cyclic compound having an organic substituent, ammonia, and air. In the first step, for example, a nitrile compound such as an aromatic nitrile compound is generated by ammoxidation reaction using the raw material gas. The reacted gas containing the nitrile compound generated in the reactor is discharged from the reactor in the second step.

(Cyclic Compound Having an Organic Substituent)

Examples of the cyclic compound having an organic substituent used in the raw material gas of the present embodiment include a carbocyclic compound or a heterocyclic compound having an organic substituent. Hereinafter, a cyclic compound having an organic substituent may be referred to as a "cyclic compound of the present embodiment".

The carbocyclic compound having an organic substituent is a carbocyclic compound having a carbocyclic ring such as benzene, naphthalene, anthracene, cyclohexene, cyclohexane, dihydronaphthalene, tetralin, and decalin, and having, as a side chain, an organic substituent, such as a methyl group, an ethyl group, a propyl group, a formyl group, an acetyl group, a hydroxymethyl group, and a methoxycarbonyl group. The carbocyclic compound may further comprise a substituent which does not participate in ammoxidation reaction such as a halogen group, a hydroxyl group, an alkoxy group, a phenyl group, an amino group, and a nitro group.

Specific examples of the carbocyclic compound having an organic substituent include toluene, xylene, trimethylbenzene, ethylbenzene, methylnaphthalene, dimethylnaphthalene, methyltetralin, dimethyltetralin, chlorotoluene, dichlorotoluene, methylaniline, cresol, and methyl anisole.

The heterocyclic compound having an organic substituent is a heterocyclic compound having the above organic substituent on a heterocyclic ring such as furan, pyrrole, indole, thiophene, pirazole, imidazole, oxazole, pyrane, pyridine, chinoline, isochinoline, pyrroline, pyrrolidine, imidazoline, imidazolidine, piperidine, and piperazine. Furthermore, similarly to the above carbocyclic compound, the heterocyclic compound may have a substituent not participating in ammoxidation reaction as a side chain.

Specific examples of a heterocyclic compound having an organic substituent include furfural, 2-methylthiophene, 3-methylthiophene, 2-formylthiophene, 4-methylthiazol, methylpyridine, dimethylpyridine, trimethylpyridine, methylchinolin, methylpyrazine, dimethylpyrazine, and methylpiperazine. These compounds may be used alone or in the form of a mixture.

The manufacturing method of the present embodiment is particularly preferably applied to a method in which meta-xylene having two methyl groups on a benzene ring is used as the above cyclic compound and isophthalonitrile which is an aromatic nitrile compound is manufactured as a nitrile compound generated using the cyclic compound.

The concentration of the cyclic compound of the present embodiment in the raw material gas of the present embodiment is preferably 0.2 to 10 vol %, more preferably 0.5 to 5 vol % from the viewpoint of the yield and space time yield of the nitrile compound. When the present embodiment is implemented, the concentration of the cyclic compound of the present embodiment is preferably 0.07 moles or less as the number of moles of the organic substituent based on 1 mole of all components supplied to the reactor. The number of moles of the organic substituent based on 1 mole of all components supplied to the reactor represents a value obtained by multiplying the concentration by volume of the compound having an organic substituent and the number of the organic substituent contained in the compound having an organic substituent. For example, 1.5 vol % of xylene (having two methyl groups as organic substituents) gives an organic substituent concentration of 0.015×2=0.03 moles based on 1 mole of all components supplied to the reactor.

"vol %" in the present embodiment means a ratio of volume under so-called standard conditions at 0° C. and 1 atm.

(Catalyst)

As described above, in the manufacturing method of the present embodiment, a raw material gas is supplied in the presence of a catalyst and a nitrile compound is manufactured by gas phase catalytic ammoxidation reaction. Examples of a reaction system of ammoxidation reaction include reaction systems such as a fixed bed, moving bed, and fluidized bed, but a fluidized bed system is preferably used from the viewpoint of control of the reaction temperature, the cost of an apparatus, etc. The catalyst used in the present embodiment is not particularly limited as long as it is an ammoxidation catalyst suitable for gas phase catalytic reaction. As the catalyst, for example, a catalyst containing an oxide of at least one element selected from vanadium, molybdenum, and iron is preferably used. In the case of a fluidized bed catalyst used for a fluidized bed system, the particle size of the catalyst is preferably within the range of 10 to 300 µm, and the average particle size is within the range of 30 to 200 µm, preferably 40 to 100 µm. The bulk density of the catalyst is preferably within the range of 0.5 to 2 g/cm$^3$, preferably 0.7 to 1.5 g/cm$^3$.

(Ammonia)

Ammonia contained in the raw material gas of the present embodiment is not particularly limited, but industrial grade ammonia can be used. When the amount of ammonia to be used is too small, the yield of the nitrile compound reduces; on the other hand, when the amount of ammonia to be used is too large, an industrial disadvantage results from loss of unreacted ammonia or increase in cost of recovery. From such a viewpoint, the amount of ammonia to be used is preferably within such range that the molar ratio of ammonia to the organic substituents contained in the cyclic compound of the present embodiment in the raw material gas ($NH_3$/organic substituent) is 1 to 10 times by mole, preferably 3 to 7 times by mole.

In the present embodiment, the configuration may be provided wherein a nitrile compound which is the objective substance is separated from the reacted gas discharged through a reactor outlet, then mist in the residual gas component (the first residual gas) after separation is removed to obtain the second residual gas, which is then resupplied to the ammoxidation reactor. When ammonia is contained in the first and second residual gas in a non-negligible amount, the amount of freshly supplied ammonia may be appropriately adjusted.

(Air)

In the manufacturing method of the present embodiment, air is used as an oxygen source. When the amount of air to be used is too small, the yield of the nitrile compound reduces, and when the amount is too large, the space time yield reduces. From such a viewpoint, the amount of air to be used is preferably adjusted so that the molar ratio of oxygen to the organic substituents contained in the cyclic compound of the present embodiment in the raw material gas ($O_2$/organic substituent) is within the range of 1.5 to 7 times by mole, preferably 1.5 to 5 times by mole.

(Ammoxidation Reaction)

The reaction pressure of ammoxidation conducted in a reactor in the presence of a catalyst may be normal pressure, increased pressure, or reduced pressure, but is preferably within the range from around normal pressure to 0.2 MPa. The contact time of the raw material gas with the catalyst depends on conditions such as the type of the cyclic compound of the present embodiment, the composition of the supplied raw material, and the reaction temperature, but is usually within the range of 0.5 seconds to 30 seconds.

In the reaction of the raw material gas in the presence of a catalyst in the reactor, when the reaction temperature is low, a sufficient reaction rate cannot be obtained. On the other hand, when the reaction temperature is too high, production of byproducts such as carbon dioxide and hydrogen cyanide increases and the yield of the nitrile compound reduces. From such a viewpoint, the above reaction temperature is usually about 300 to 500° C., preferably within the range of 330 to 470° C. Preferably, the above reaction temperature is appropriately selected as a temperature which provides an optimum yield, while considering the activity of the catalyst, etc. under the above operating condition.

[Second Step]

The second step is a step of discharging a reacted gas from the reactor and separating the nitrile compound form the reacted gas. "Reacted gas" in the present embodiment means a gas containing at least a nitrile compound generated in the reactor. Furthermore, the reacted gas containing the nitrile compound generated in the reactor in the first step contains "residual gas components" such as ammonia, hydrogen cyanide, carbon dioxide, water, carbon monoxide, nitrogen, oxygen, and a cyclic compound such as an unreacted carbocyclic compound or a heterocyclic compound in addition to the nitrile compound.

The second step is, for example, conducted in a nitrile collection column, etc. described below. The gas obtained by separating the nitrile gas in the second step is transferred as the first residual gas to the third step which is the next step.

(Separation of Nitrile Compound)

Examples of a method of separating and collecting a nitrile compound from a reacted gas include a method (1) in which a reacted gas is contacted with an organic solvent which can dissolve a nitrile compound and the nitrile compound is collected in the solvent to be separated from the residual gas component, and a method (2) in which a reacted gas is cooled and a nitrile compound is deposited as a solid or condensed as a liquid to be separated from the residual gas component.

In the case of the above method (1), an organic solvent such as an alkylbenzene, a heterocyclic compound, an aromatic nitrile, and a heterocyclic nitrile is used as an organic solvent. Using the nitrile compound generated in ammoxidation reaction as the organic solvent is advantageous because the kinds of substances to be handled do not increase. In the manufacturing method of the present embodiment, for example, when isophthalonitrile is obtained using meta-xylene as a cyclic compound of the present embodiment, metatolunitrile generated as a byproduct in ammoxidation reaction can be preferably used as a catalyst.

[Third Step]

The third step is a step of collecting mist from a first residual gas obtained by separating the nitrile compound from the reacted gas to remove water and ammonium carbonate in the first residual gas. In the present embodiment, "first residual gas" means a gas containing the above residual gas components and obtained by separating the nitrile compound from the reacted gas. However, the first residual gas may contain the nitrile compound which has not been separated in the second step.

The first residual gas contains nitrogen as a main component, and in addition, contains ammonia, hydrogen cyanide, carbon dioxide, water, carbon monoxide, oxygen, cyclic compounds such as an unreacted carbocyclic compound or a heterocyclic compound, and the like, which are the above residual gas components. The temperature of the first residual gas containing carbon dioxide and ammonia and obtained by separating the nitrile compound is generally lower than that of the reacted gas, and in a temperature lower than or equal to the thermal decomposition temperature of ammonium carbonate, ammonium carbonate having high solubility in water is likely to generate. Ammonium carbonate in the first residual gas is usually contained in the first residual gas in the state of being dissolved in mist-form water.

Furthermore, in the manufacturing method of the present embodiment, for example, a step of contacting the first residual gas with water and collecting ammonia and hydrogen cyanide contained in the first residual gas may be provided after the second step and before the third step.

In the third step, mist is collected from the first residual gas. In the present embodiment, "mist" means liquid particles and is not particularly limited, but it is usually formed by condensation of steam, spraying of liquid, or the like, and it means liquid particles having a particle size of 0.01 μm to several tens of m. In the third step, water existing as mist in the first residual gas is collected, and thus ammonium carbonate dissolved in the water can be removed along with water. In addition to ammonium carbonate, the mist may contain carbon dioxide and ammonia which are components constituting ammonium carbonate. The first residual gas usually contains water as mist due to entrainment phenomenon, but the amount of mist in the first residual gas may be controlled by adjusting pressure and temperature in the reactor, etc.

On the other hand, for example, when isophthalonitrile is manufactured using xylene, a large amount of water is generated by the reaction. The water generated by the reaction is likely to be in the form of mist when the gas flow rate is high. Since water in the mist form is likely to be entrained by a circulating gas, it is difficult to be discharged to the outside of the reaction system compared to the case of a water droplet which has a large size to some extent, and thus it is likely to be retained in the reaction system. On the other hand, in the manufacturing method of the present embodiment, the mist is directly collected in the third step, and thus the amount of the mist existing in the reaction system can be reduced, and an effect of suppressing deposition of ammonium carbonate can be more enhanced.

In the third step, "collecting mist" differs from means for recovering mist as comparatively large liquid particles such as water droplets by controlling the temperature and pressure of the first residual gas, for example, a cooling apparatus, and it means collecting mist by a mechanism such as inertial collision against a collector, diffusion, shielding, and gravity. As means for collecting mist from the first residual gas, for example, a mist eliminator can be used.

(Mist Eliminator)

A "mist eliminator" is also referred to as a mist separator, and is an apparatus having a mist collecting mechanism which utilizes inertial collision against a collector, diffusion, shielding, gravity, etc. Examples of the mist eliminators include a mesh type, Vane-type, and candle-type mist eliminators, and a commonly known mist eliminator can be used. These mist eliminators can be also classified depending on the collecting method to be used (for example, inertial collision against a collector, diffusion due to Brownian motion of mist, and gravity). For example, a mesh-type and Vane-type mist eliminator utilizes inertial collision against a collector, and a candle-type mist eliminator utilizes Brownian motion. As the mist eliminator, a known mist eliminator can be appropriately selected and used, and when a mist eliminator is used for industrial manufacturing of a nitrile compound, a Vane-type mist eliminator can be preferably used which can be adapted to a large gas flow rate. A Vane-type mist eliminator is a mist eliminator utilizing inertial collision against a collector, and can be preferably used under the condition in which high load and high flow rate are required. The principle of a mist eliminator (separator) and other details are described in, for example, "Mist separator no seino to sono ouyou (in Japanese) (Performance of mist separator and application thereof)" K. Okuyama (Kankyo Gijyutsu (in Japanese) (Environmental Engineering), 2 (11), pp. 824-830, 1973).

[Other Steps]

The manufacturing method of the present embodiment may comprise a step of resupplying the second residual gas to the above reactor, the second residual gas being obtained by removing the water and the ammonium carbonate from the first residual gas in the third step. In the present embodiment, "the second residual gas" means the first residual gas from which mist has been collected in the third step. The second residual gas contains at least oxygen, and in addition, contains carbon dioxide, carbon monoxide, nitrogen, oxygen, a cyclic compound such as an unreacted carbocyclic compound or heterocyclic compound, etc. Furthermore, the second residual gas may contain the nitrile compound and water which have not been removed in the second and the third step.

When the second residual gas is resupplied to the reactor, the amount of the second residual gas supplied to the reactor is preferably 10 to 60 vol %, more preferably 15 to 50 vol % based on the amount of the raw material gas freshly supplied through the reactor inlet from the viewpoint of an effect of stabilizing the oxygen concentration in the supplied gas, the circulating amount, and the space time yield.

In the present embodiment, the second residual gas is resupplied to the reactor.

[Flow of Manufacturing Method of the Present Embodiment]

Hereinafter, the flow of the manufacturing method of the present embodiment will be described with reference to FIG. 1. FIG. 1 is a schematic view showing an example of the manufacturing process of a nitrile compound of the present embodiment.

In the manufacturing method of the present embodiment shown in FIG. 1, ammoxidation reaction is conducted by fluidized bed reaction, the reacted gas discharged from the reactor is contacted with a solvent to conduct collecting, and the first residual gas after collecting is further contacted with water to collect ammonia. After that, mist is removed from the first residual gas by a mist eliminator, then the second residual gas is resupplied to the ammoxidation reactor.

In FIG. 1, the manufacturing apparatus used for the manufacturing method of the present embodiment comprises an ammoxidation reactor 1, a nitrile collection column 2, a water washing column 3, and a mist eliminator 4. A fluidized bed catalyst is filled in the ammoxidation reactor 1. A raw material gas containing the cyclic compound of the present embodiment, ammonia, and air, and the residual gas for resupplying (the second residual gas) are supplied to the ammoxidation reactor 1 to conduct ammoxidation reaction. A cooling pipe is provided inside the reactor, and the fluidized bed catalyst is provided so that the interface of the fluidized bed catalyst layer is under the upper end of the cooling pipe. After catalyst particles are separated from the raw material gas using a catalyst cyclone, which is not shown, and the raw material gas is returned to the fluidized bed catalyst layer via a return pipe, the raw material gas is discharged as the reacted gas through a discharging pipe. The reacted gas discharged from the ammoxidation reactor 1 contains a nitrile compound, ammonia, hydrogen cyanide, carbon dioxide, water, carbon monoxide, nitrogen, oxygen, an unreacted cyclic compound of the present embodiment, etc., and is transferred to the nitrile collection column 2 of the next step. In the nitrile collection column 2, the reacted gas is contacted with a solvent to collect the nitrile compound contained in the reacted gas, and thus the nitrile compound is separated from the reacted gas. The first residual gas after collecting the nitrile is transferred to the water washing column 3 of the next step. In the water washing column 3, the residual gas is contacted with water to collect ammonia and hydrogen cyanide contained in the first residual gas. Then, the first residual gas is supplied to the mist eliminator, and mist in the gas is collected to remove water and ammonium carbonate from the first residual gas. The second residual gas discharged from the mist eliminator is resupplied to the ammoxidation reactor 1 as a gas for resupplying. The apparatus may be configured so that a part of the second residual gas is supplied to the ammoxidation reactor 1, and the rest of the second residual gas is transferred to a waste gas treatment facility such as an incinerator.

Hereinabove, the present invention has been described with reference to the embodiments, but these embodiments are examples and do not limit the present invention.

EXAMPLES

Hereinafter, the present invention will be described more specifically with reference to Examples. However, the present invention is not limited to these Examples. The result of the reaction in the Examples below is a ratio based on meta-xylene as a raw material.

Example 1

<Preparation of Catalyst>

An aqueous solution of chromic acid was prepared by dissolving 196 g of chromic anhydride $CrO_3$ in 200 mL of pure water.

Then, an aqueous solution of oxalic acid was prepared by adding 600 mL of pure water to 753 g of oxalic acid and heating the obtained mixture to 50° C. to 60° C. To this aqueous solution of oxalic acid with stirring, the aqueous solution of chromic acid was gradually added to prepare an aqueous solution of chromium oxalate.

Then, after dissolving 444 g of oxalic acid in 400 mL of pure water and heating the obtained mixture to 80 to 90° C., 178 g of vanadium pentoxide $V_2O_5$ was gradually added to the mixture while sufficiently stirring to prepare an aqueous solution of vanadyl oxalate. Furthermore, the aqueous solution of chromium oxalate prepared as described above was added dropwise to and mixed with the aqueous solution of vanadyl oxalate prepared as described above at 70° C. to 90° C. 12.1 g of boric acid was added to and mixed with this mixed aqueous solution at 70° C. to 90° C. The thus prepared catalyst solution was heated to 85° C. to 95° C. and subjected to aging. Then, the solution was concentrated at 100° C. to 110° C. 1333 g of titanium oxide of anatase-type was added to the concentrated liquid formulation, and the formulation was kneaded using a kneader at 70° C. until it became uniform while water was evaporated. Then, the obtained cake was dried by a dryer at 110° C.

Then, the dried product was pre-baked in a baking furnace at 400° C. for 2 hours, then pulverized by a pulverizer. 4% by mass of Graphite was added to and mixed with the pulverized powder. Then this raw material powder was formed into a tablet using a tablet molding machine so that a ring-shaped tablet having outer diameter of 5.7 mm, inner diameter of 2.4 mm, and height of 5.8 mm was obtained. After molding, the tablet was baked in a baking furnace at 600° C. for 15 hours. The atomic ratio of this catalyst was Cr:V:B=1.0:1.0:0.1, and the concentration of titania support in the catalyst was 80% by mass.

<Manufacturing of Nitrile Compound>

Figure 2:
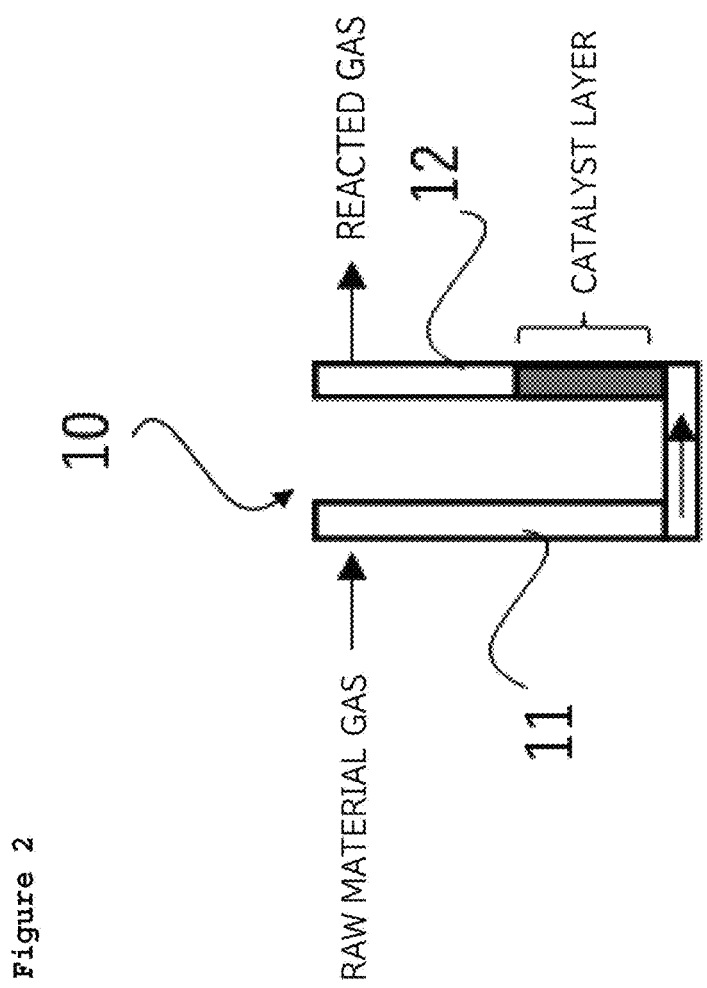
FIG. 2 is a schematic view showing the structure of the reactor of the present embodiment.

As shown in FIG. 2, downward flow part of the inlet side 11 of the reaction tube 10 was a preheating layer, upward flow part of the outlet side 12 of the reaction tube 10 was a catalyst layer. Then, the catalyst obtained as described above was fractured into 8 pieces using pliers, then sieved with a 1.25 mm mesh, and subsequently sieved with a 0.95 mm mesh to prepare the fractured catalyst A having a size of 0.95 to 1.25 mm. 10 g of fractured catalyst A was filled over the whole catalyst layer.

A reaction tube was installed in a fused salt bath maintained at 400° C., an inlet side tube and an outlet side tube of the reaction tube were heated and heat-retained by a heater. As raw materials, 1.95 g/hr of meta-xylene, 2.45 g/hr of ammonia, 155 Nml/min of air, and 390 Nml/min of nitrogen were introduced into the reaction tube at normal pressure and subjected to catalytic reaction. The reacted gas was absorbed by tetrahydrofuran, and "GC-2010" gas chromatograph manufactured by SHIMADZU CORPORATION and a column "DB-1" (length 60 m, thickness 0.25 micrometer, inner diameter 0.25 mm (manufactured by Agilent Technologies, Inc.)) were used with tridecane as an internal standard, and a column temperature of 120° C. was retained for 5 minutes under the conditions of 15 ml/min of helium carrier, an inlet temperature of 235° C., a split ratio of 11, detector FID, 235° C. After that, the column temperature was increased by 40° C./min up to 230° C. and retained for 10 minutes, and analysis was conducted under the condition of 1 microliter of injection volume. As results of analysis, the conversion ratio of meta-xylene was 90%, the yield of isophthalonitrile was 60%.

Then, isophthalonitrile was absorbed by passing the reacted gas through 30 ml of m-tolunitrile.

Furthermore, water was removed from the gas after removing isophthalonitrile (the first residual gas) using a mist separator having filtration rating of 40 μm (product name, BN-2720-8 manufactured by NIPPON SEIKI CO., LTD.).

After that, the obtained gas (the second residual gas) was passed through 50 cm Teflon® tube having an inner diameter of 6 mm.

After conducting reaction for 15 minutes, as a result of checking the Teflon tube, white powder was adhered to the tube. The tube was washed with 30 ml of water, and the white powder was recovered. The washing water used for recovery was subjected to titration with 0.1 mol/L aqueous solution of hydrochloric acid using neutralization titration apparatus "COM-1700" manufactured by HIRANUMA SANGYO Co., Ltd.

As a result, the initial pH was 9, and a curve having two stages was obtained. As a result of checking the amount of recovered ammonium carbonate using the peak of the second stage, 0.004 mol of ammonium carbonate was confirmed.

Comparative Example 1

Isophthalonitrile was produced similarly to Example 1 except that a mist separator was not used. The content of ammonium carbonate was measured for the finally obtained gas similarly to Example 1.

The amount of ammonium carbonate recovered from Teflon tube was 0.01 mol.

Unlike the Example, a large amount of white powder was adhered to the Teflon tube, and there was a concern about clogging.

The disclosure of Japanese Patent Application No. 2019-065750 filed on Mar. 29, 2019 is herein incorporated by reference in its entirety.

All literatures, patent applications, and engineering standards described in the specification are incorporated herein by reference to the same extent as the case in which it is shown specifically and individually that individual literature, patent application, and engineering standard are incorporated by reference.

REFERENCE SIGNS LIST 1 ammoxidation reactor
2 nitrile collection column
3 water washing column
4 mist eliminator
10 reactor
11 downward flow part of the inlet side
12 upward flow part of the outlet side

The invention claimed is:

1. A method of manufacturing a nitrile compound, comprising:
   introducing a raw material gas comprising a cyclic compound having an organic substituent, ammonia, and air into a reactor such that the raw material gas reacts in a presence of a catalyst and generates a nitrile compound;
   discharging a reacted gas from the reactor;
   separating the nitrile compound from the reacted gas such that a first residual gas is obtained; and
   collecting mist from the first residual gas such that water and ammonium carbonate are removed from the first residual gas.

2. The method of claim 1, wherein the collecting of the mist is conducted by a mist eliminator.

3. The method of claim 2, wherein the mist eliminator is a Vane-type mist eliminator.

4. The method of claim 1, wherein the cyclic compound is a carbocyclic compound or a heterocyclic compound.

5. The method of claim 1, wherein the nitrile compound is an aromatic nitrile compound.

6. The method of claim 1, wherein the cyclic compound is meta-xylene, and the nitrile compound is isophthalonitrile.

7. The method of claim 1, further comprising:
   resupplying to the reactor a second residual gas obtained by the removing of the water and the ammonium carbonate from the first residual gas.

8. The method of claim 7, wherein the resupplying includes supplying the second residual gas in an amount of 10 to 60 vol % based on the raw material gas freshly supplied through an inlet of the reactor.

9. The method of claim 2, wherein the cyclic compound is a carbocyclic compound or a heterocyclic compound.

10. The method of claim 3, wherein the cyclic compound is a carbocyclic compound or a heterocyclic compound.

11. The method of claim 2, wherein the nitrile compound is an aromatic nitrile compound.

12. The method of claim 4, wherein the nitrile compound is an aromatic nitrile compound.

13. The method of claim 2, wherein the cyclic compound is meta-xylene, and the nitrile compound is isophthalonitrile.

14. The method of claim 4, wherein the cyclic compound is meta-xylene, and the nitrile compound is isophthalonitrile.

15. The method of claim 5, wherein the cyclic compound is meta-xylene, and the nitrile compound is isophthalonitrile.

16. The method of claim 2, further comprising:
   resupplying to the reactor a second residual gas obtained by the removing of the water and the ammonium carbonate from the first residual gas.

17. The method of claim 3, further comprising:
   resupplying to the reactor a second residual gas obtained by the removing of the water and the ammonium carbonate from the first residual gas.

18. The method of claim 4, further comprising:
   resupplying to the reactor a second residual gas obtained by the removing of the water and the ammonium carbonate from the first residual gas.

19. The method of claim 5, further comprising:
   resupplying to the reactor a second residual gas obtained by the removing of the water and the ammonium carbonate from the first residual gas.

20. The method of claim 6, further comprising:
   resupplying to the reactor a second residual gas obtained by the removing of the water and the ammonium carbonate from the first residual gas.

* * * * *